(12) United States Patent
Lee

(10) Patent No.: US 12,011,464 B2
(45) Date of Patent: Jun. 18, 2024

(54) COMPOSITION COMPRISING INDUCED EXOSOME FOR HAIR REGENERATION

(71) Applicant: STEMON INC., Seongnam-si (KR)

(72) Inventor: Yong Seung Lee, Suwon-si (KR)

(73) Assignee: STEMON INC., Seongnam-si (KR)

( * ) Notice: Subject to any disclaimer, the term of this patent is extended or adjusted under 35 U.S.C. 154(b) by 644 days.

(21) Appl. No.: 17/276,230

(22) PCT Filed: Sep. 19, 2019

(86) PCT No.: PCT/KR2019/012134
§ 371 (c)(1),
(2) Date: Mar. 15, 2021

(87) PCT Pub. No.: WO2020/071662
PCT Pub. Date: Apr. 9, 2020

(65) Prior Publication Data
US 2022/0040238 A1     Feb. 10, 2022

(30) Foreign Application Priority Data

Oct. 2, 2018     (KR) .................... 10-2018-0117263

(51) Int. Cl.
| | |
|---|---|
| *A61K 35/36* | (2015.01) |
| *A61P 17/14* | (2006.01) |
| *C12N 5/071* | (2010.01) |
| *C12N 13/00* | (2006.01) |

(52) U.S. Cl.
CPC .............. *A61K 35/36* (2013.01); *A61P 17/14* (2018.01); *C12N 5/0625* (2013.01); *C12N 13/00* (2013.01); *C12N 2529/00* (2013.01)

(58) Field of Classification Search
None
See application file for complete search history.

(56) References Cited

FOREIGN PATENT DOCUMENTS

| | | |
|---|---|---|
| KR | 10-1425653 B1 | 8/2014 |
| KR | 10-2017-0020245 A | 2/2017 |
| KR | 10-2017-0044999 A | 4/2017 |
| KR | 10-2017-0106149 A | 9/2017 |
| KR | 10-1781526 B1 | 9/2017 |
| KR | 10-2018-0015994 A | 2/2018 |
| KR | 10-1836029 B1 | 3/2018 |
| KR | 10-2018-0060317 A | 6/2018 |
| KR | 10-1894229 B1 | 9/2018 |

*Primary Examiner* — Michael V Meller
(74) *Attorney, Agent, or Firm* — Bridgeway IP Law Group, PLLC; Jihun Kim

(57) ABSTRACT

A method for producing exosomes comprises steps of: providing ultrasound stimulation directly or indirectly to cells; culturing a mixture of the cells and a medium for a predetermined time; and isolating exosomes from the mixture, wherein providing the stimulation directly to the cells comprises applying ultrasound stimulation to the medium containing the cells, and the providing the stimulation indirectly to the cells comprises applying ultrasound stimulation to the medium not containing the cells and then mixing the medium and the cells. This method for producing exosomes makes it possible to obtain exosomes having a hair regeneration effect not only from stem cells and progenitor cells that are difficult to isolate and multiply, but also from somatic cells that may be easily obtained and maintained, in high yield within a short time by ultrasound treatment that is a simple process.

8 Claims, 17 Drawing Sheets

Amount of read counted mRNA
contained in exosomes

| Gene Symbol | Reprosome | HDF.Exo |
|---|---|---|
| Ptc1 | 19 | 0 |
| TCF3 | 21 | 0 |
| VCAN | 15 | 0 |
| B-catenin | 20 | 0 |
| Shh | 17 | 0 |
| KRT25 | 12 | 0 |
| Gli1 | 3 | 0 |
| Lef1 | 7 | 0 |
| Mitf | 1 | 0 |
| Tyr | 1 | 0 |
| Tyrp1 | 3 | 0 |
| DCT | 3 | 0 |

FIG. 4C

COMPOSITION COMPRISING INDUCED EXOSOME FOR HAIR REGENERATION

TECHNICAL FIELD

The present invention relates to exosomes having a hair regeneration effect, a production method therefor and a composition containing the exosomes.

BACKGROUND ART

Hair goes through a certain hair cycle consisting of: the anagen phase when stimulated keratinocytes in dermal papilla actively divide and proliferate and the hair grows; the catagen phase when blood supply to the hair bulb is cut off and the dermal papilla is separated from the hair follicle; and the telogen phase when cell proliferation stops and the hair does not grow. After the telogen phase, the hair enters the anagen phase again or enters the exogen stage when the hair comes out of the scalp. Human hairs follow independent growth cycles, and enter the exogen phase on one side but enter the anagen phase on the other hand so that the total number of hairs will be uniformly maintained. Alopecia refers to a condition in which this balance is shifted to the exogen phase so that the hair is lost in the area where the hair should normally exist.

Alopecia causes serious mental pain to the corresponding persons, and in recent years, interest in alopecia has increased as the age group at which alopecia symptoms occur has decreased. The causes of hair loss are diverse and broadly include internal factors such as male hormone degeneration, autoimmunity, endocrine diseases, childbirth, menopause, and aging, and external factors such as nutritional deficiencies, drugs, stress, scalp contamination, scalp dryness, and *Acarus folliculorum*.

In order to ameliorate this hair loss phenomenon, many kinds of hair loss amelioration agents or hair growth inducing agents have been developed. There are currently no proven treatments other than minoxidil and finasteride among the drug treatments approved by the US Food and Drug Administration (FDA), and these two synthetic drugs are effective only when they are taken continuously, and thus have problems of side effects due to long-term exposure, cost ineffectiveness, and inconvenience. In addition, among these, finasteride has an effect of preventing hair loss, but has an insignificant effect on the growth of hair that has been in the telogen phase for a long period of time, and it also has various side effects as a hormonal agent Biologics, which are pharmaceutical drugs based on proteins, genes, cells, etc. derived from organisms, have advantages in that they have low toxicity because they produce no metabolite in vivo, unlike synthetic drugs, exhibit good effects by selectively acting on the pathogenesis of diseases, and have fewer side effects. In recent years, as these advantages have attracted attention, methods of treating hair loss using biologics, particularly stem cells, has been developed. Korean Patent No. 10-1425653 (Aug. 5, 2014) discloses a cell therapy product for hair loss, which is obtained by mixing adipose tissue-derived adult stem cells and scalp tissue-derived hair follicle cells, and Korean Patent No. 10-1781526 (Sep. 19, 2017) discloses a hair loss treatment containing a stem cell extract, and Korean Patent No. 10-1836029 (Mar. 8, 2018) discloses a composition for preventing hair loss and promoting hair growth containing a stem cell-conditioned medium obtained by stimulation with TGF-β. However, the compositions using stem cells commonly have problems in terms of efficiency and economy due to complicated stem cell isolation and multiplication, and the stem cell therapy product has a disadvantage in that it is cost-ineffective and time-consuming because it is not easy to purify an active ingredient from cells. In addition, the stem cell-conditioned medium has a problem in that it contains wastes secreted from cells or substances that have not been verified for safety in human use, such as antibiotics added to prevent contamination and serum, in addition to containing an active ingredient.

It is known that exosomes are naturally secreted nanovesicles having a diameter of 30 to 200 nm, and can act as important nanomediators that deliver various substances from cells. Since the discovery that exosomes can change the phenotype of target cells through mRNA delivery, several studies have revealed that exosomes are involved in cell differentiation and the like. In recent years, the possibility of applying exosomes directly to the human body for therapeutic purposes has been explored in various ways. In particular, exosomes may exhibit more complex and long-lasting effects in the biologics field, because they contain a variety of proteins and nucleic acids compared to biopharmaceuticals such as small molecules, peptides, growth factors, antibodies, nucleic acids, etc. In addition, exosomes do not cause risk of development into cancer, unlike large-sized medicines such as cells, and may advantageously have spatiotemporal effects different from those of cells because they do not require degradation into vesicles, which occurs when cells are injected. In recent years, in particular, technology of using exosomes, obtained from stem cells known to have effects of ameliorating and treating various symptoms, as therapeutic compositions, has been developed. Korean Patent Application Publication No. 10-2017-0044999 (Oct. 16, 2015) discloses a composition for preventing or treating hair loss containing, as an active ingredient, exosomes derived from adult stem cells or a conditioned medium thereof. However, it is difficult to mass-produce exosomes through technologies related to therapeutic compositions using exosomes, including the technology of the above-described patent application publication, and these technologies mostly use stem cells that are difficult to isolate and multiply. Therefore, in order to use exosomes clinically, there is a need for a technology capable of increasing the yield of exosomes while obtaining the exosomes from cells that may be easily obtained, multiplied and maintained, not from stem cells.

DISCLOSURE

Technical Problem

The present invention has been made in order to solve the above-described problems, and one embodiment of the present invention provides a production method capable of obtaining exosomes having a hair regeneration effect in high yield within a short time from cells from which the exosomes are easily obtainable, the method comprising steps of: providing ultrasound stimulation directly or indirectly to cells; culturing a mixture of the cells and a medium for a predetermined time; and isolating exosomes from the mixture, wherein providing the stimulation directly to the cells comprises applying ultrasound stimulation to a medium containing the cells, and providing the stimulation indirectly to the cells comprises applying ultrasound stimulation to a medium not containing the cells and then mixing the medium and the cells.

Another embodiment of the present invention provides exosomes produced by the above production method, which have increased RNA of a gene that promotes hair regeneration.

Still another embodiment of the present invention provides a composition containing the exosomes, which is safe and may persistently exhibit a hair regeneration effect.

Technical problems to be achieved by the present invention are not limited to the above-mentioned technical problem, and other technical problems which are not mentioned herein will be clearly understood by those skilled in the art from the following description.

Technical Solution

As a technical means for achieving the above-described technical problem, a method for producing exosomes having a hair regeneration effect according to one aspect of the present invention comprises steps of: providing ultrasound stimulation directly or indirectly to cells; culturing a mixture of the cells and a medium for a predetermined time; and isolating exosomes from the mixture, wherein providing the stimulation directly to the cells is applying ultrasound stimulation to the medium containing the cells, and providing the stimulation indirectly to the cells is applying ultrasound stimulation to the medium not containing the cells and then mixing the medium and the cells.

Here, the step of providing ultrasound stimulation directly or indirectly to cells may be performed by any one method selected from among: a method of mixing the cells and the medium and then providing ultrasound stimulation to the mixture; or a method of providing ultrasound stimulation to the medium and then mixing the medium and the cells; or a method of providing ultrasound stimulation to the cells and then mixing the cells and the medium; or a method of providing ultrasound stimulation to the cells and then mixing the cells and the medium, followed by providing ultrasound stimulation to the mixture; or a method of providing ultrasound stimulation to the medium and then mixing the medium and the cells, followed by providing ultrasound stimulation to the mixture; or a method of providing ultrasound stimulation to each of the cells and the medium and then mixing the cells and the medium; or a method of providing ultrasound stimulation to each of the cells and the medium and then mixing the cells and the medium, followed by providing ultrasound stimulation to the mixture.

Providing the ultrasound stimulation directly to the cells may be performed at an ultrasound intensity of 0.1 to 3 W/cm$^2$ and a frequency of 20 kHz to 20 MHz for a duration of 0.1 seconds to 20 minutes, and providing the ultrasound stimulation indirectly to the cells may be performed at an ultrasound intensity of 1 to 20 W/cm$^2$ and a frequency of 20 kHz to 20 MHz for a duration of 0.1 seconds to 20 minutes.

The cells may be selected from the group consisting of mammalian stem cells, progenitor cells, fibroblasts, keratinocytes or organ tissue cells.

The medium may be any one of embryonic stem cell medium, dermal papilla cell medium, or hair follicle stem cell medium.

The culturing of the mixture may be performed for 1 hour to 10 days.

The step of isolating the exosomes may be performed using one or more of ultracentrifugation, density gradient separation, filtration, size exclusion chromatography, immunoaffinity separation, precipitation, and microfluidic separation.

The step of isolating the exosomes may comprise steps of: centrifuging the mixture after the culturing to obtain a supernatant; filtering the supernatant through a filter to obtain a filtrate; and concentrating the filtrate.

The step of isolating the exosomes may further comprise a step of storing the supernatant at 4° C. or below for 7 days to 1 month before filtering the supernatant through the filter.

The isolated exosomes may have a diameter of 50 to 200 nm.

Another aspect of the present invention provides exosomes having a hair regeneration effect, which are produced by the above-described production method.

Here, the exosomes may have increased RNA of a gene that promotes hair regeneration, compared to exosomes secreted from the cells before being subjected to the above-described production method, wherein the gene that promotes hair regeneration may be any one or more of β-catenin, Shh, KRT25, Lef1, VCAN, Ptc1, Tcf3, Mitf, Tyr, Tyrp1, Gli1 and Dct.

The exosomes, when applied to the skin, may further increase RNA expression of a gene that promotes hair regeneration in the skin, and further decrease RNA expression of a gene that inhibits hair regeneration, compared to the exosome secreted from the cells before being subjected to the above-described production method, wherein the gene that promotes hair regeneration may be any one or more of Shh, β-catenin, KRT25, VCAN, Gli1, Lef1, Ptc1, Tyrp1, Tyr, Mitf and Dct, and the gene that inhibits hair regeneration may be any one or more of Sfrp4 and DKK.

Still another aspect of the present invention provides a composition containing the above-described exosomes having a hair regeneration effect.

Here, the composition may contain the exosomes at a concentration of $10^6$ exosomes/ml or more.

The above-described means for solving the problem is merely exemplary and should not be construed as limiting the present invention. In addition to the above-described exemplary embodiments, additional embodiments may exist in the drawings and the detailed description of the invention.

Advantageous Effects

The method for producing exosomes according to one embodiment of the present invention may induce secretion of a large amount of exosomes having a hair regeneration effect not only from stem cells and progenitor cells that are difficult to isolate and multiply, but also from easily available somatic cells, within a short time by ultrasound treatment that is a simple process. The exosomes thus induced are obtained in higher yield than those in a conventional method, and the amount and number of various factors contained in the exosomes are also large.

The exosomes according to one embodiment of the present invention and a composition containing the same contain large amounts of various factors capable of inducing hair regeneration, particularly RNAs of genes that promote hair regeneration. In addition, the exosomes have a phospholipid-based membrane structure, and thus may easily penetrate the scalp and deliver substances with high efficiency, thus effectively inducing hair regeneration. Moreover, the exosomes have no side-effects occurring due to the use of synthetic drugs, and advantageously have a longer-lasting effect.

It is to be understood that the effects of the present invention are not limited to the above-described effects, and include all effects that may be deduced from the features described in the detailed description of the invention or the claims.

DESCRIPTION OF DRAWINGS

FIG. 4A, FIG. 4B and FIG. 4C show RT-qPCR data obtained by analyzing the hair regeneration-related mRNA in exosomes having a hair regeneration effect according to Example 1 of the present invention.

BEST MODE

Figure 1A:
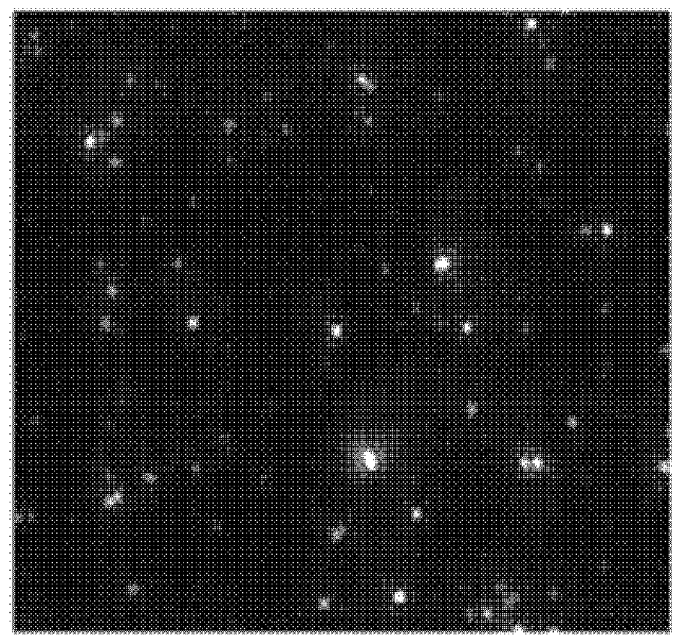
FIG. 1A, FIG. 1B, FIG. 1C and FIG. 1D show data related to the production of exosomes having a hair regeneration effect according to Example 1 of the present invention, depicts nanosight and electron microscope images (a and b) showing the shape of the exosomes, and shows the sizes and concentrations (c and d) of the exosomes produced according to Example 1 and a control group (HDF-exo).

Hereinafter, the present invention will be described in more detail. However, the present invention may be embodied in various different forms and is not limited by the embodiments described herein, and the scope of the present invention should be defined only by the appended claims.

The terminology used herein is only for the purpose of describing particular embodiments and is not intended to be limiting of the present invention. Singular expressions include plural expressions unless otherwise specified in the context thereof. Throughout the present specification, it is to be understood that when any part is referred to as "comprising" any component, it does not exclude other components, but may further comprise other components, unless otherwise specified.

A method for producing exosomes having a hair regeneration effect according to one aspect of the present invention comprises steps of: providing ultrasound stimulation directly or indirectly to cells; culturing a mixture of the cells and a medium for a predetermined time; and isolating exosomes from the mixture, wherein providing the stimulation directly to the cells comprises applying ultrasound stimulation to a medium containing the cells, and providing the stimulation indirectly to the cells comprises applying ultrasound stimulation a medium not containing the cells and then mixing the medium and the cells.

Here, the step of providing ultrasound stimulation directly or indirectly to cells may be performed by any one method selected from among: a method of mixing the cells and the medium and then providing ultrasound stimulation to the mixture; or a method of providing ultrasound stimulation to the medium and then mixing the medium and the cells; or a method of providing ultrasound stimulation to the cells and then mixing the cells and the medium; or a method of providing ultrasound stimulation to the cells and then mixing the cells and the medium, followed by providing ultrasound stimulation to the mixture; or a method of providing ultrasound stimulation to the medium and then mixing the medium and the cells, followed by providing ultrasound stimulation to the mixture; or a method of providing ultrasound stimulation to each of the cells and the medium and then mixing the cells and the medium; or a method of providing ultrasound stimulation to each of the cells and the medium and then mixing the cells and the medium, followed by providing ultrasound stimulation to the mixture. The ultrasound stimulation may be performed may be provided directly or indirectly to the cells one or more times or provided using a combination of one or more selected from the above methods, and as the number of times increases, the hair regeneration effect of exosomes may increase proportionally. When the ultrasound stimulation is provided one or more times as described above, it is preferable to provide a time interval between the provisions so that the cells can recover, and the time interval may be at least 1 day, more preferably at least 2 days.

Providing the ultrasound stimulation directly to the cells may be performed at an ultrasound intensity of 0.1 to 3 W/cm$^2$ and a frequency of 20 kHz to 20 MHz for a duration of 0.1 seconds to 20 minutes, and providing the ultrasound stimulation indirectly to the cells may be performed at an ultrasound intensity of 1 to 20 W/cm$^2$ and a frequency of 20 kHz to 20 MHz for a duration of 0.1 seconds to 20 minutes. More preferably, providing the ultrasound stimulation directly to the cells may be performed at an ultrasound intensity of 0.5 to 2 W/cm$^2$ and a frequency of 20 kHz to 2 MHz for a duration of 0.1 seconds to 10 minutes, and providing the ultrasound stimulation indirectly to the cells may be performed at an ultrasound intensity of 2 to 10 W/cm$^2$ and a frequency of 20 kHz to 2 MHz for a duration of 1 second to 15 minutes.

The cells may be selected from among mammalian cells excluding mammalian germ cells. Preferably, the cells may be selected from the group consisting of mammalian stem cells, progenitor cells, fibroblasts, keratinocytes, or organ tissue cells, and more preferably, may be any one type of mammalian fibroblasts or organ tissue cells. This is because the method for producing exosomes having a hair regeneration effect according to one aspect of the present invention makes it possible to obtain the exosomes using any type of cells, and thus cells that are easy to obtain, maintain and multiply are easier and more efficient than stem cells or progenitor cells, which are difficult to obtain and difficult to multiply. The cells may be either autologous, allogeneic or heterologous depending on the future use of the exosomes in vivo as described below. When the cells are heterologous, the cells may be of mammalian origin. Since there is a possibility for an immune rejection reaction, preferably the cells may be allogeneic, most preferably autologous. In order to reduce the likelihood of immune rejection, the cells are preferably allogeneic cells, most preferably autologous cells.

The step of providing ultrasound stimulation to the cells may be performed either by directly treating the cells with ultrasound or in a state in which only a minimum amount of the cells are contained in an initial culture medium so that the cells barely covers the initial culture medium. Here, the initial culture medium is a common medium used to maintain the cells in a healthy state, and may be a medium suitable for normal culture of the cells. For example, the cells may be fibroblasts, and the initial culture medium may be DMEM medium containing antibiotics and serum.

The culture medium (a medium that is treated with ultrasound without cells) may be selected from among embryonic stem cell medium, dermal papilla cell medium, and hair follicle stem cell medium, but is not limited thereto. For example, the culture medium may be any one of embryonic stem cell medium, mesenchymal stem cell medium, neural stem cell medium, adipose stem cell medium, hematopoietic stem cell medium, dermal papilla cell medium, and hair follicle stem cell medium. The invention of Korean Patent Application No. 10-2018-0060317 filed in the name of present inventor discloses that, when exosomes are obtained by culturing a mixture of an ultrasound-treated second cell culture medium (a medium capable of culturing second cells or inducing differentiation into second cells) and ultrasound-treated first cells and other cells are treated with the exosomes, the cells may be reprogrammed into the second cells, and that stem cells or extracts or conditioned media thereof all exhibit an effect on the treatment of hair loss.

The culturing of the mixture may be performed for 1 to 10 days, preferably 1 to 6 days, most preferably 1 to 2 days. This is because exosomes are secreted in the largest amount on day 1 after ultrasound treatment, and their secretion decreases over time, and this decrease in secretion indicates a possibility that there is a change in the components.

The step of isolating the exosomes may be performed using one or more of ultracentrifugation, density gradient separation, filtration, size exclusion chromatography, immunoaffinity separation, precipitation, and microfluidic separation.

The step of isolating the exosomes may comprise steps of: centrifuging the mixture after the culturing to obtain a supernatant; filtering the supernatant through a filter to obtain a filtrate; and concentrating the filtrate. The centrifugation is performed to remove cell debris and dead cells, and may preferably be performed at 1,000 to 5,000 g for 10 to 60 minutes. The step of filtering the supernatant through the filter is performed to further remove cellular debris and obtain only particles having a specific size or less, and the filter used herein may be preferably a syringe filter. The step of concentrating the filtrate may preferably be performed using a centrifugal filter. Where the centrifugal filter is used, it is possible to remove particles having a specific size or less while concentrating the filtrate. The step of isolating the exosomes may further comprise a step of storing the supernatant at 4° C. or below for 7 days to 3 months before filtering the supernatant through the filter. The storage may preferably be done at 4° C. or less for 7 days or less, more preferably −20° C. or less for 1 month or less, most preferably −80° C. or less for 3 months or less. The active ingredients of the exosomes include mRNA and protein, and these ingredients may be more easily denatured or degraded as the temperature is higher or closer to the temperature at which the enzyme activity is high.

The isolated exosomes may have a diameter of 50 to 200 nm, preferably 100 to 150 nm.

Exosomes having a hair regeneration effect according to another aspect of the present disclosure may be produced by the above-described production method.

Here, the exosomes have increased RNA of a gene that promotes hair regeneration, compared to exosomes secreted from the cells before being subjected to the method of claim 1, wherein the gene that promotes hair regeneration may be any one or more of β-catenin (beta-catenin), Shh (sonic hedgehog), KRT25 (keratin 25), Lef1 (lymphoid enhancer binding factor 1), VCAN (versican), Ptc1 (patched 1), TCF3 (transcription factor 3), MITF (microphthalmia-associated transcription factor), Tyr (tyrosinase), Tyrp1 (tyrosinase related protein 1), Gli1 (GLI family zinc finger 1) and Dct (dopachrome tautomerase).

The exosomes, when applied to the skin, may further increase RNA expression of a gene that promotes hair regeneration in the skin, and further decrease RNA expression of a gene that inhibits hair regeneration, compared to the exosome secreted from the cells before being subjected to the above-described production method, wherein the gene that promotes hair regeneration may be any one or more of Shh (sonic hedgehog), β-catenin (beta-catenin), KRT25 (keratin 25), VCAN (versican), Gli1 (GLI family zinc finger 1), Lef1 (lymphoid enhancer binding factor 1), Ptc1 (patched 1), Tyrp1 (tyrosinase related protein 1), Tyr (tyrosinase), MITF (microphthalmia-associated transcription factor) and Dct (dopachrome tautomerase), and the gene that inhibits hair regeneration may be any one or more of Sfrp4 (secreted frizzled related protein 4) and DKK (Dickkopf).

Still another aspect of the present invention provides a composition containing the exosomes having a hair regeneration effect.

Here, the composition may contain the exosomes at a concentration of at least $10^6$ exosomes/ml, more preferably $10^{12}$ exosomes/ml. This is because if the concentration of exosomes in the composition is less than $10^6$ exosomes/ml or more than $10^{12}$ exosomes/ml, the hair regeneration effect may decrease, and in particular, if the concentration is excessively high, the economic efficiency may also decrease.

It is obvious that the composition may further contain a pharmaceutically acceptable carrier, and other additives that can further enhance the hair regeneration effect by increasing the penetration rate of the exosomes into the treatment site, in addition to the exosomes, and thus detailed description of the pharmaceutically acceptable carrier and other additives will be omitted.

MODE FOR INVENTION

Hereinafter, examples of the present invention will be described in detail so that the present invention can be easily carried out by those skilled in the art. However, the present invention may be embodied in various different forms, and is not limited to the examples described herein.

All cell culture processes in the Examples and Experimental Examples of the present invention were performed at 37° C. under 5% $CO_2$.

Example 1. Production of Exosomes Having Hair Regeneration Effect and Induction of Hair Regeneration Using the Same To obtain exosomes having a hair regeneration effect, ultrasound stimulation with 20 KHz and 1.0 W/cm² was applied directly to $1 \times 10^6$ human dermal fibroblasts (HDFs) for 5 seconds by means of UltraRepro 1001 (STEMON Inc., Seoul, Republic of Korea). $2 \times 10^5$ UHDFs (the HDFs to which ultrasound stimulation was applied) were cultured with an ultrasound-treated (at 20 KHz and 5.0 W/cm² for 10 min) dermal papilla cell medium (PromoCell) in a 35-mm Petri dish for one day. Exosomes were isolated from the conditioned medium of the UHDFs as follows: The conditioned medium was centrifuged at 3,000×g for 20 minutes to remove cell debris and dead cells, and then the supernatant was passed through a 0.22-mm filter (Minisart® Syringe Filter, Sartorius, Goettingen, Germany). The medium that passed through the filter was placed in Amicon® Ultra-15 100,000 kDa device (Millipore, Billerica, MA, USA) and centrifuged at 14,000×g for 20 minutes to concentrate exosomes (iExo).

Figure 1B:
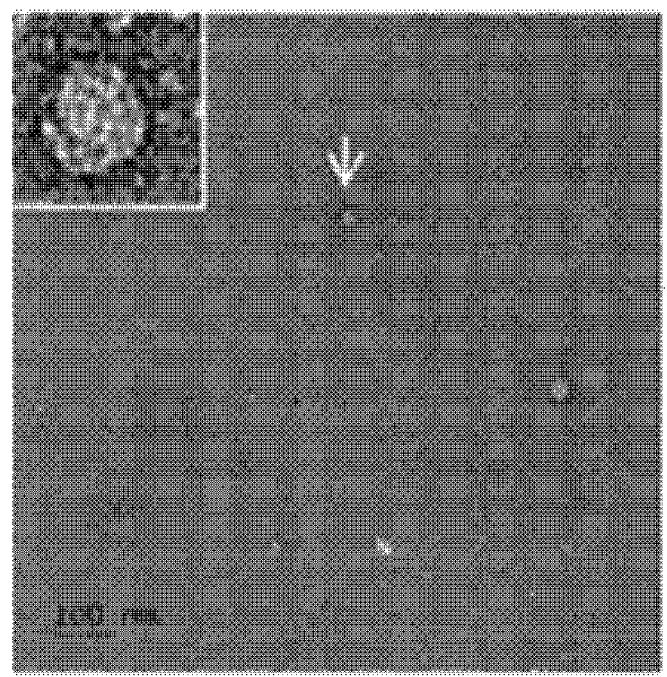
Figure 1C:
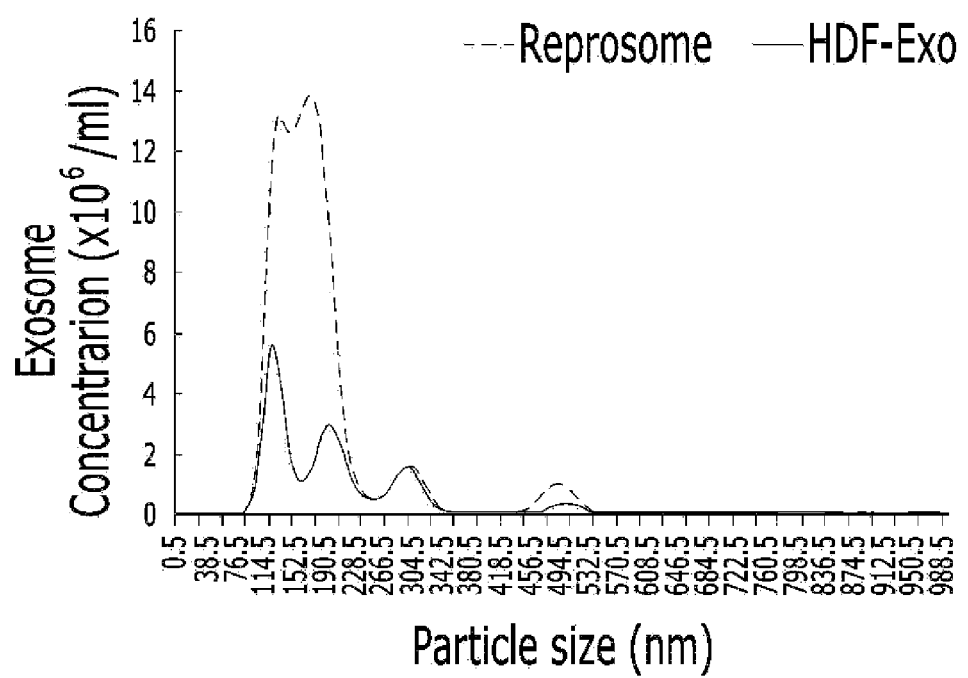
Figure 1D:
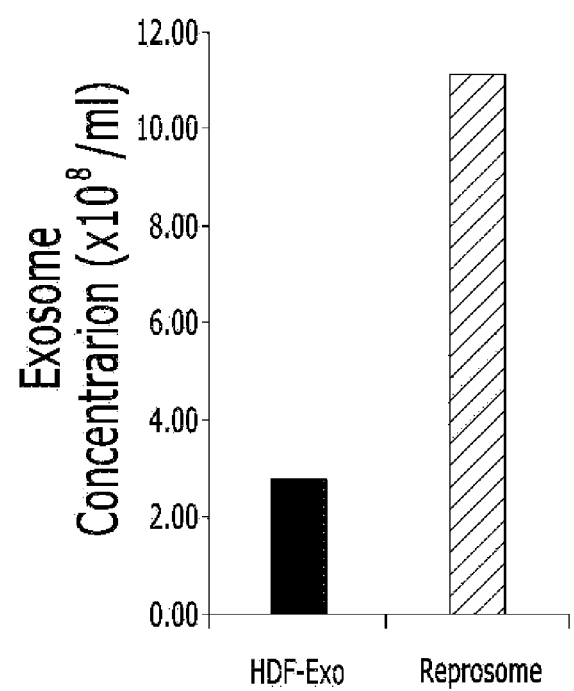
Figure 2A:
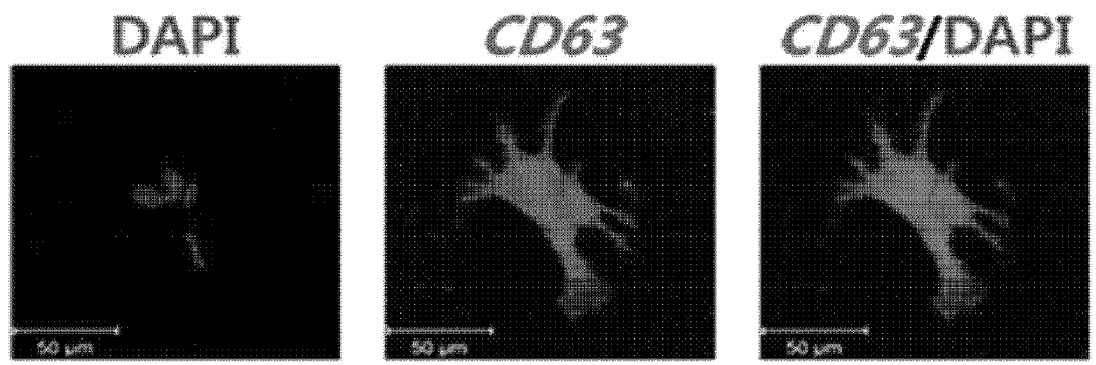
FIG. 2A and FIG. 2B show data related to the production of exosomes having a hair regeneration effect according to Example 1 of the present invention, and depicts immunofluorescence staining image showing the induction of the exosome marker CD63 and the coexistence of CD63 and Shh that is an important protein for hair regeneration.
Figure 2B:
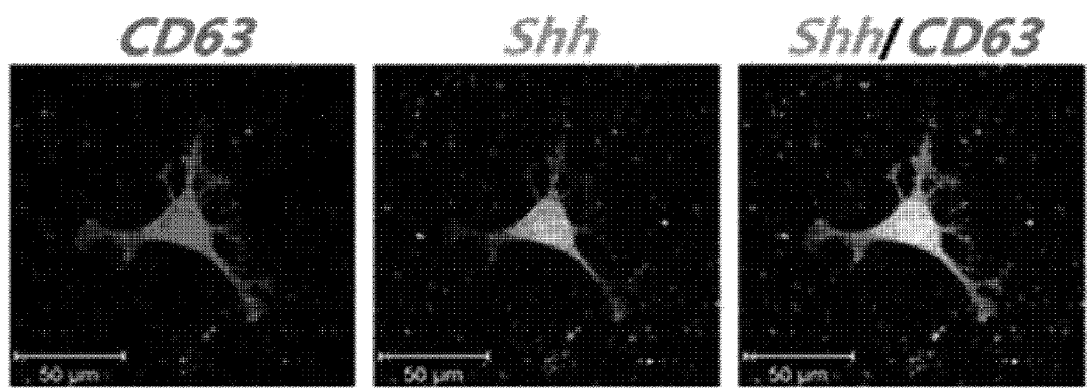
Figure 3:
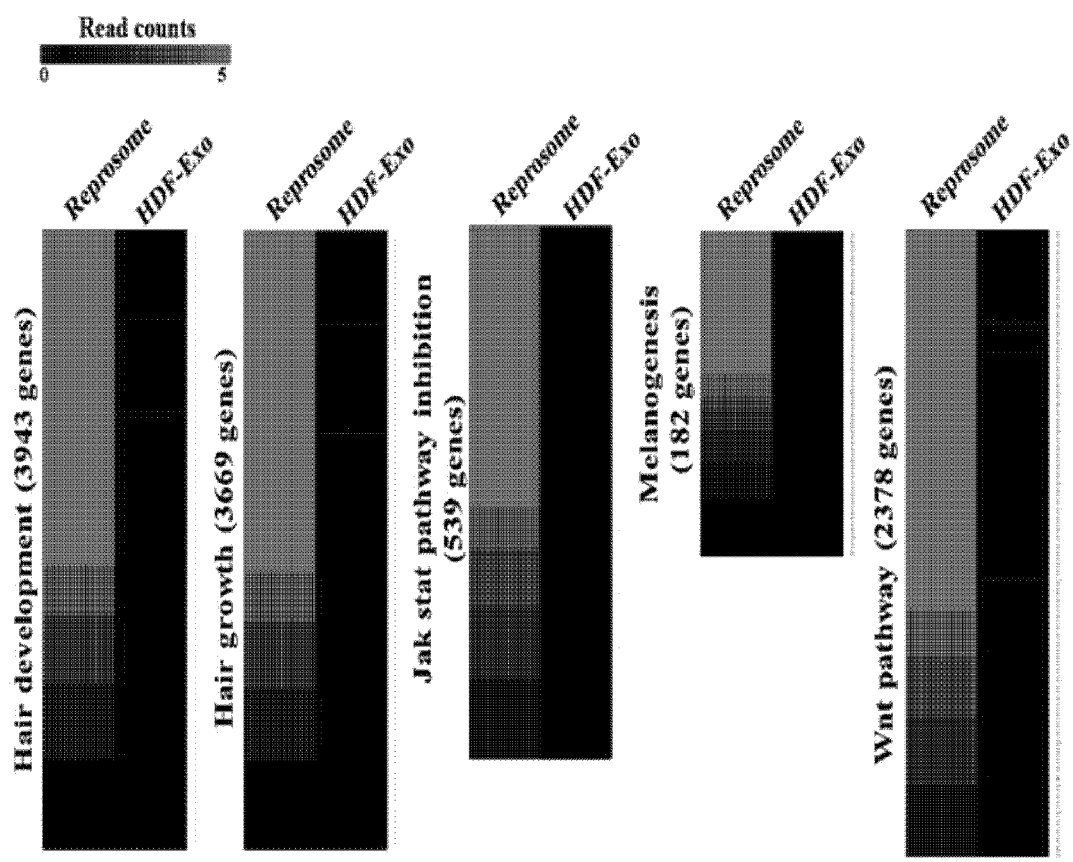
FIG. 3 shows RNA-seq data obtained by analyzing the hair regeneration-related mRNA in exosomes having a hair regeneration effect according to Example 1 of the present invention.
Figure 4A:
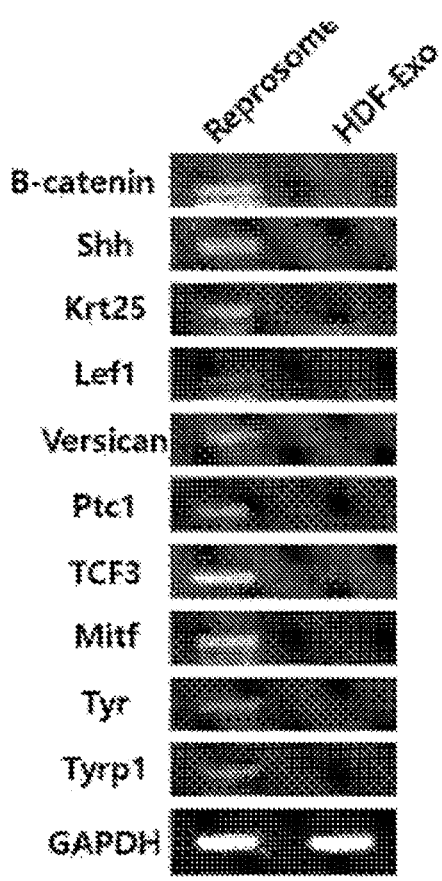
Figure 4B:
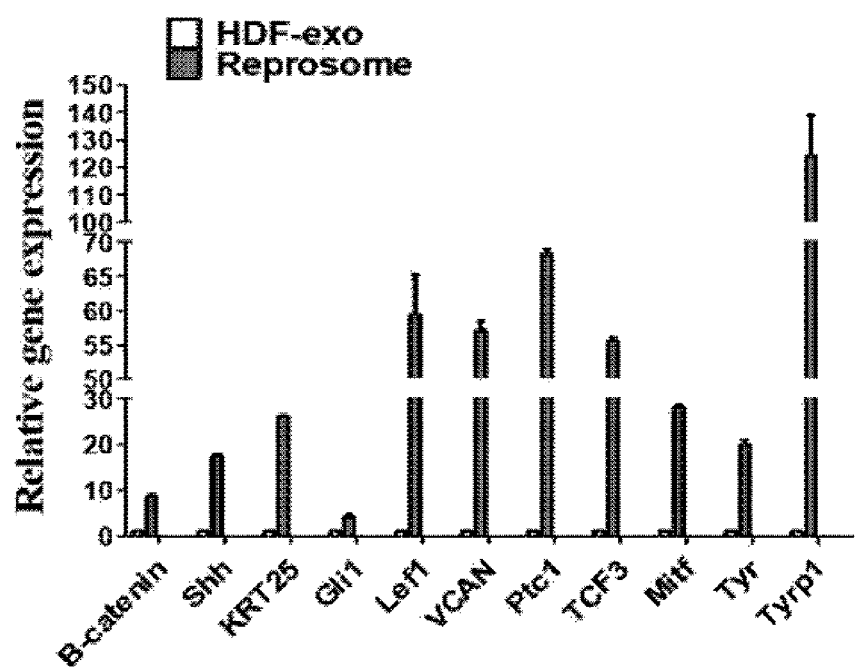

Experimental Example 1. Experiment for Analysis of Exosomes Having Hair Regeneration Effect The UHDFs cultured according to the method of Example 1 for inducing exosomes having a hair regeneration effect were analyzed through immunofluorescence staining for the CD63 exosome marker (at this time, counter staining was performed using the nuclear staining dye DAPI). As a result, it could be confirmed that a large amount of exosomes were produced (FIG. 2A). As a result of immunofluorescence staining for the marker and Shh (sonic hedgehog) which is an important marker of hair regeneration, it could be confirmed that Shh was expressed in the secreted exosomes 2B). The shape of the exosomes obtained according to the method of Example 1 for producing exosomes having a hair regeneration effect was analyzed using nanosight microscopy and TEM (transmission electron microscopy), and as a result, it was observed that the exosomes had a normal shape (FIGS. 1A and 1B). It was shown that the exosomes produced according to Example 1 generally had a diameter of 50 nm to 250 nm (FIG. 1C), and the number thereof was 4 times larger than the number of exosomes secreted from the cells which were not subjected to the above-described production method (FIG. 1D). As a result of RNA-Seq analysis for the exosomes, it was shown that mRNAs and microRNAs involved in hair tissue development, hair growth, melanogenesis, Jak-Stat signaling pathway inhibition and Wnt signaling pathway, which are associated with hair regeneration, significantly increased compared to those in the control group (FIG. 3). As a result of analyzing the exosome mRNAs by real-time PCR, it could be confirmed that β-catenin, Shh, KRT25, Lef1, versican, Ptc1, TCF3, Mitf, Tyr, Gli1 and Tyrp1 increased compared to those in the control group (FIGS. 4A and 4B). This could also be confirmed from read count analysis following RNA-seq analysis for these mRNAs (FIG. 4C). Taken together, it can be confirmed that exosomes having hair regeneration ability were successfully induced from HDFs by the exosome production method of Example 1.

Figure 5:
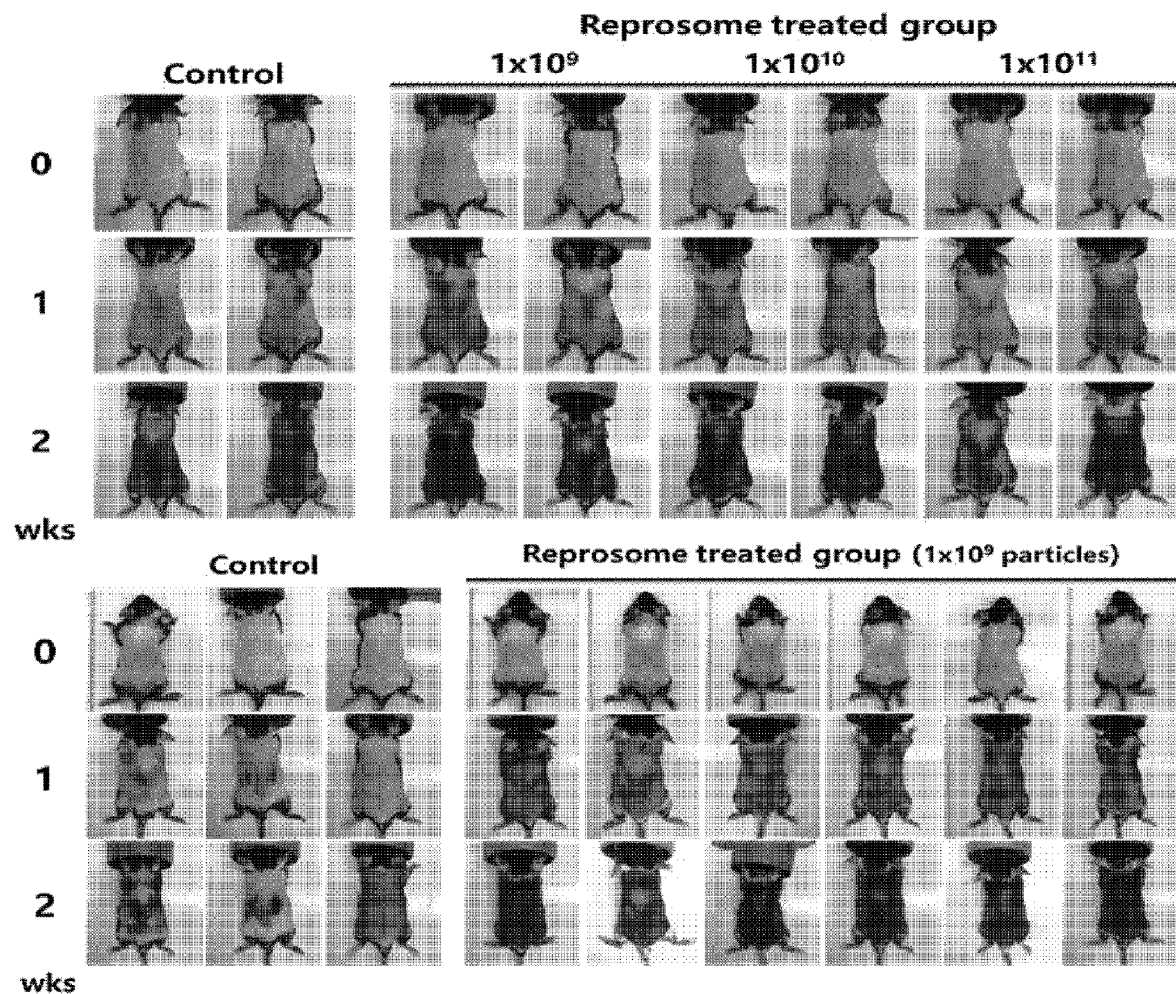
FIG. 5 depicts data showing hair regeneration in the C57 mouse skin by exosomes having a hair regeneration effect according to Example 1 of the present invention, and depicts hair regeneration images depending on the treatment concentration of the exosomes and post-treatment time.
Figure 6:
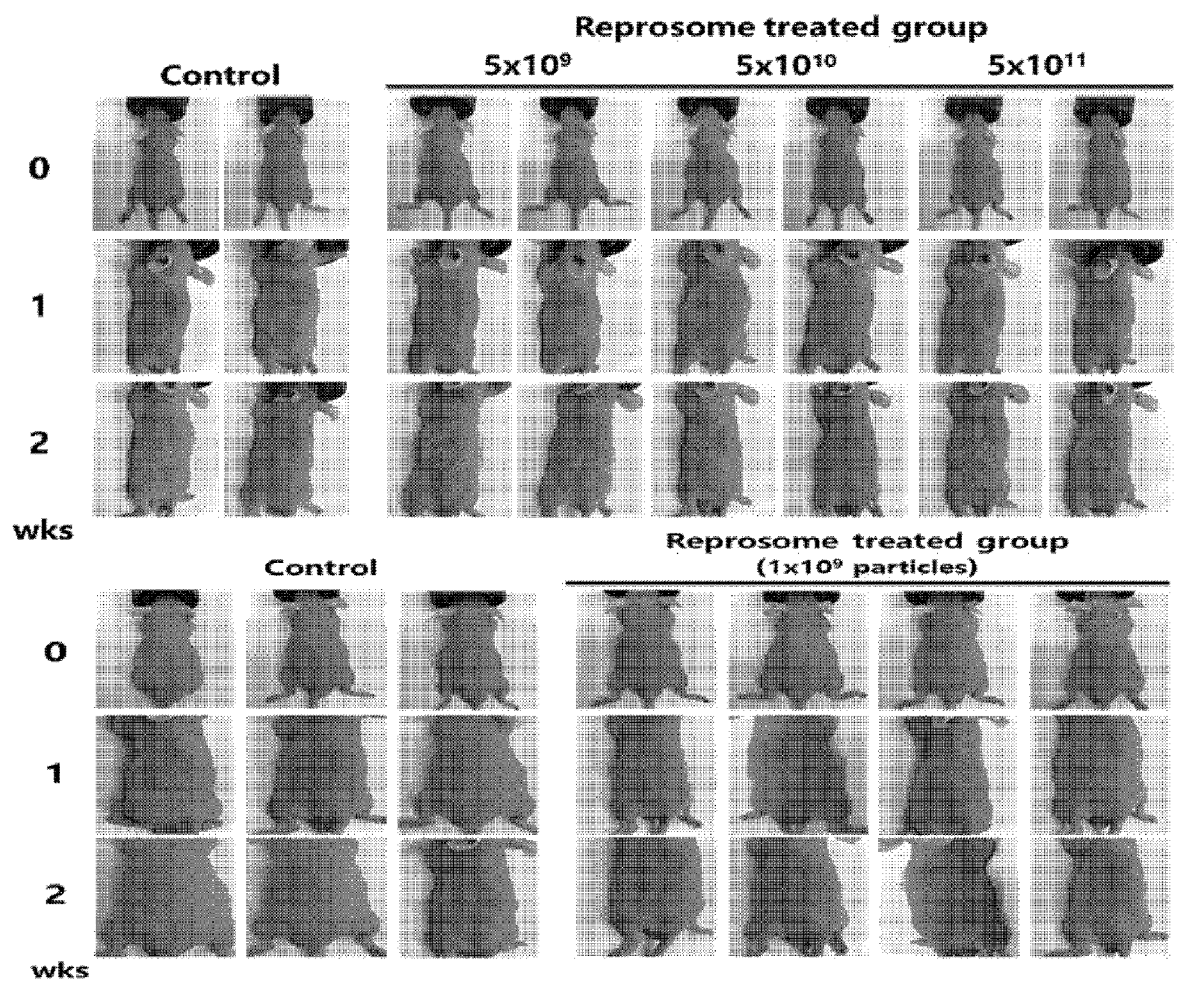
FIG. 6 depicts data showing hair regeneration in the nude mouse skin by exosomes having a hair regeneration effect according to Example 1 of the present invention, and depicts hair regeneration images depending on the treatment concentration of the exosomes and post-treatment time.

Experimental Example 2. Experiment on Hair Regeneration Using Exosomes Having Hair Regeneration Effect The exosomes obtained according to the method of Example 1 for producing exosomes having a hair regeneration were diluted in D-PBS medium and applied to the shaved dorsal side skin of C57 mice and the skin of nude mice once a week at concentrations of $1 \times 10^9$ exosomes/ml, $1 \times 10^{10}$ exosomes/ml and $1 \times 10^{11}$ exosomes/ml, and after 1 week and 2 weeks, the effect thereof was evaluated. As a result, it could be confirmed that, in the C57 mice treated with the exosomes, a larger number of hairs grew longer than those in the control group (FIG. 5). In the case of the nude mice, it could be confirmed that, in the group not treated with the exosomes, hair was not visible, whereas, in the group treated with the exosomes, a large number of hairs grew from week 1 (FIG. 6). In addition, hair in the mouse group treated with the exosomes for 2 weeks grew more than 3 times longer than that in the control group (data not shown). This demonstrates that the exosomes have a hair regeneration effect. At the same time, from the fact that hair regeneration in the nude mouse whose hair does not grow originally could be induced by applying the exosomes thereto once a week, the exosomes may have higher persistence than FDA-approved drugs that exhibit an effect only when applied twice a day.

Figure 7A:
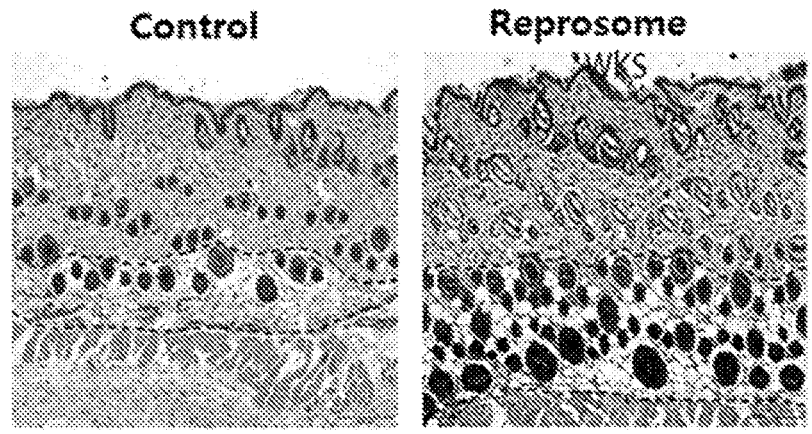
FIG. 7A and FIG. 7B depict data showing tissue changes in the skins of C57 and nude mice by exosomes having a hair regeneration effect according to Example 1 of the present invention, and shows H & E staining images of the skin tissue.
Figure 7B:
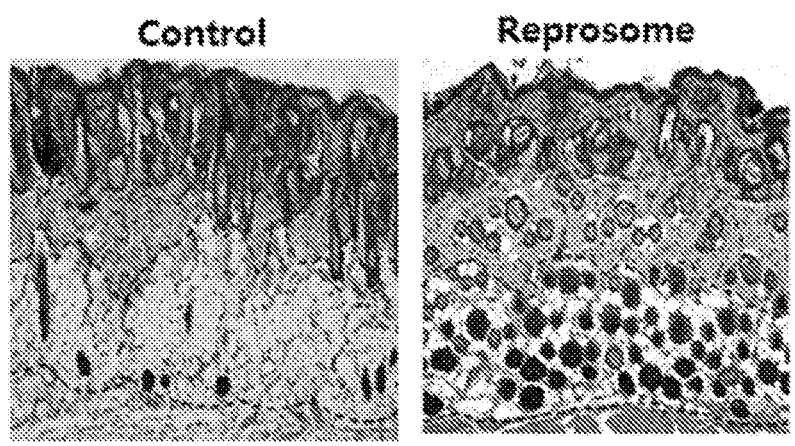
Figure 8A:
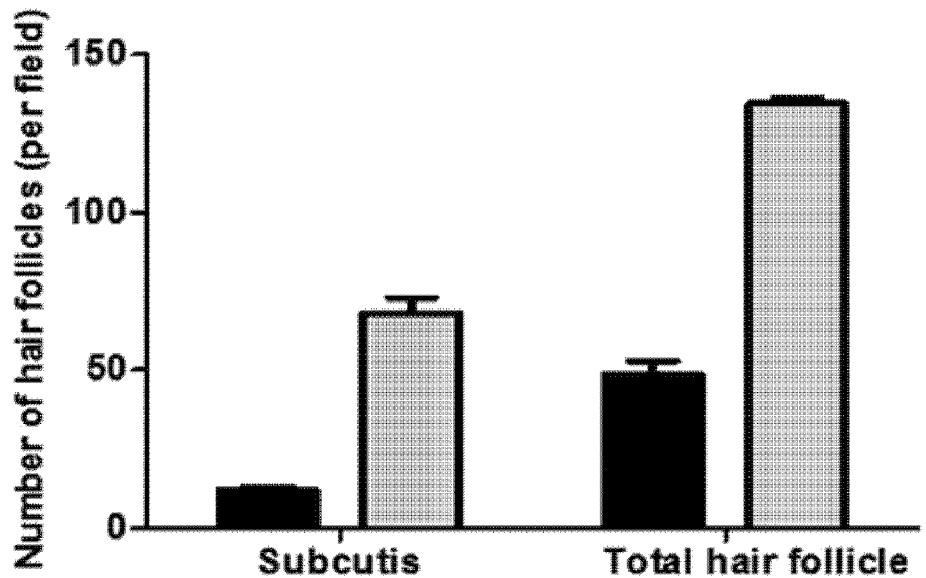
FIG. 8A and FIG. 8B depict data showing tissue changes in the skins of C57 and nude mice by exosomes having a hair regeneration effect according to Example 1 of the present invention, and depicts the number of hair follicles in subcutis and total skin tissue.
Figure 8B:
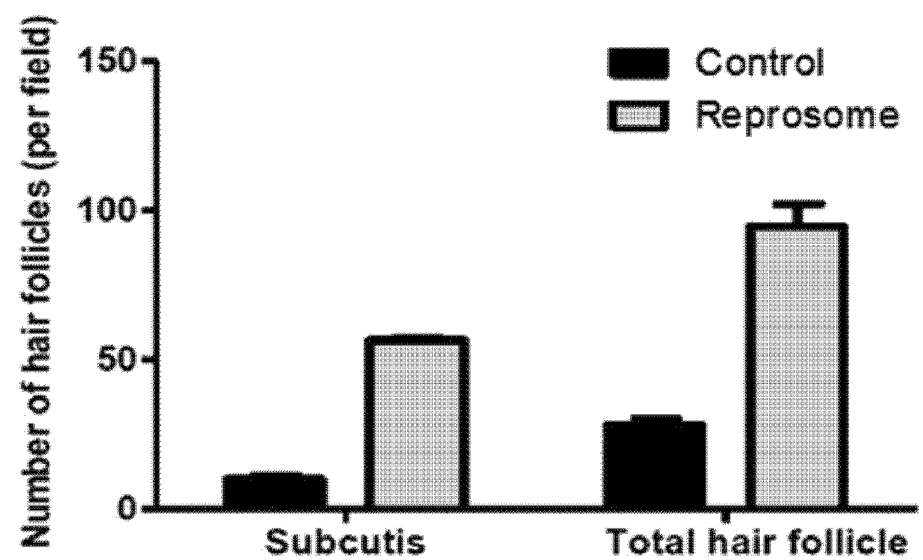
Figure 9A:
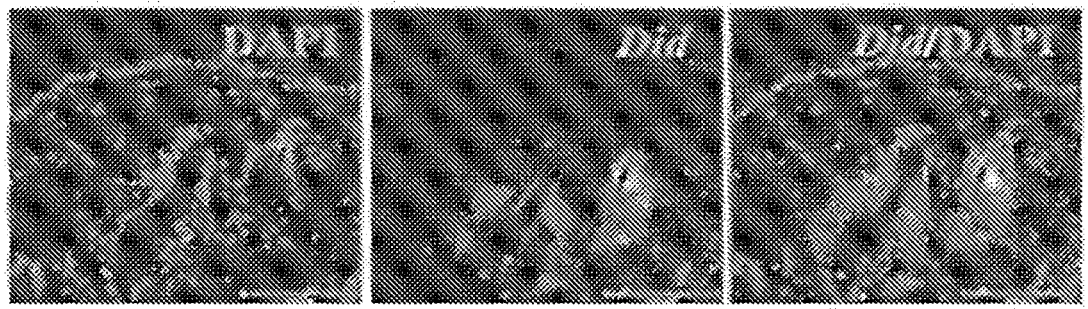
FIG. 9A and FIG. 9B depict data showing in vivo gene expression changes in the C57 mouse skin by exosomes having a hair regeneration effect according to Example 1 of the present invention, and depicts fluorescence staining images showing the distribution after skin application of the exosomes labeled with the lipophilic marker Did, and protein immunofluorescence staining images related to the changed in expression of hair follicle regeneration gene by treatment with the exosomes.
Figure 9B:
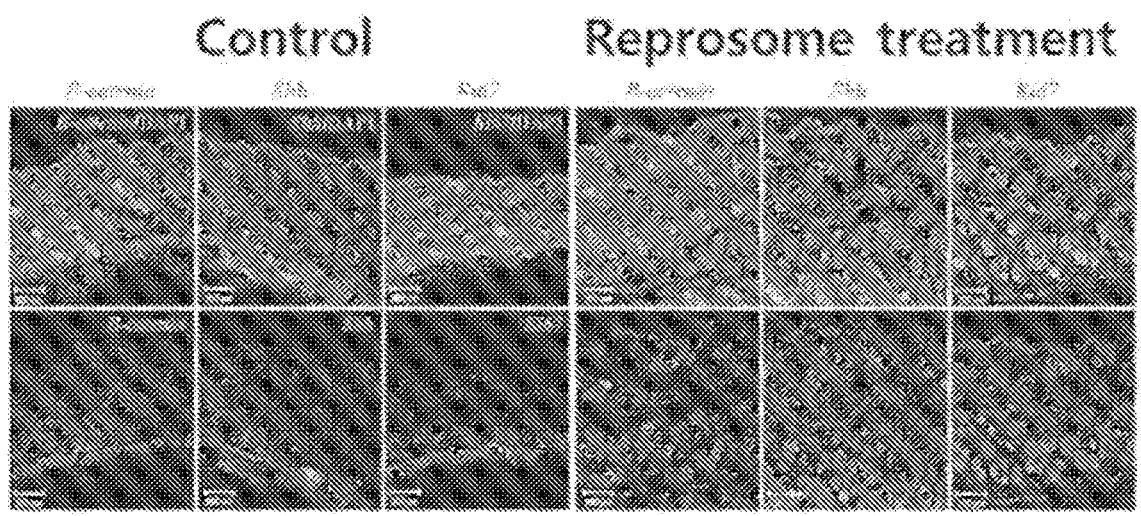
Figure 10:
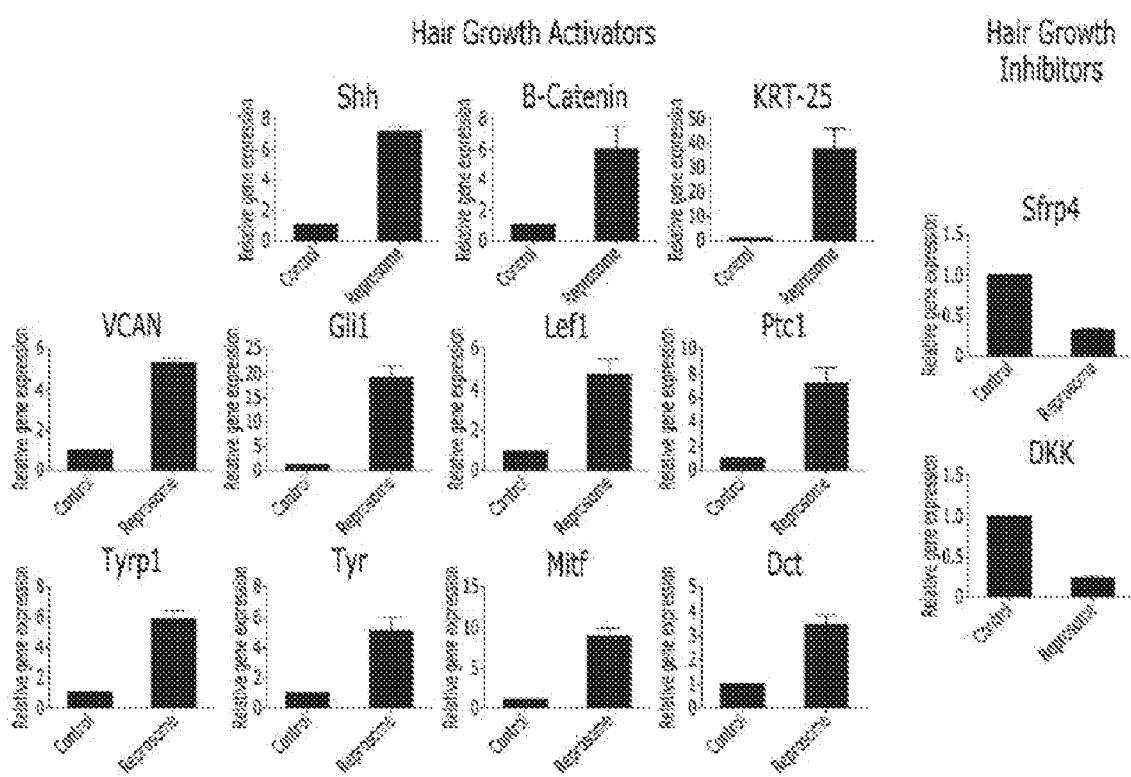
FIG. 10 depicts data showing in vivo gene expression changes in the C57 mouse skin by exosomes having a hair regeneration effect according to Example 1 of the present invention, and shows mRNA qRT-PCR data related to the changes in expression of hair follicle regeneration genes by treatment with the exosomes.
Figure 11A:
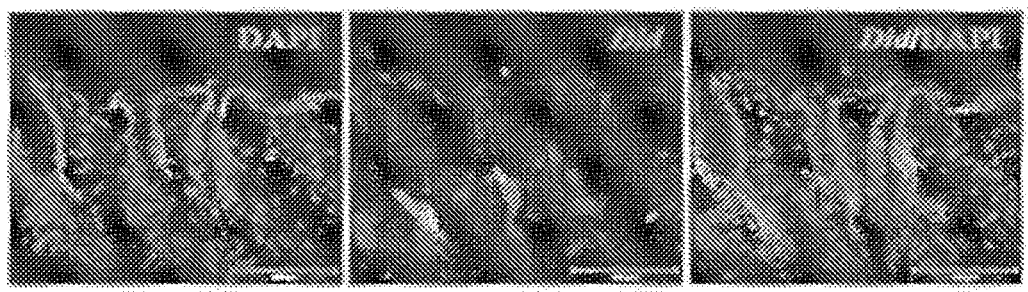
FIG. 11A and FIG. 11B depict data showing in vivo gene expression changes in the nude mouse skin by exosomes having a hair regeneration effect according to Example 1 of the present invention, and depicts fluorescence staining images showing the distribution after skin application of the exosomes labeled with the lipophilic marker Did, and protein immunofluorescence staining images related to the changed in expression of hair follicle regeneration gene by treatment with the exosomes.
Figure 11B:
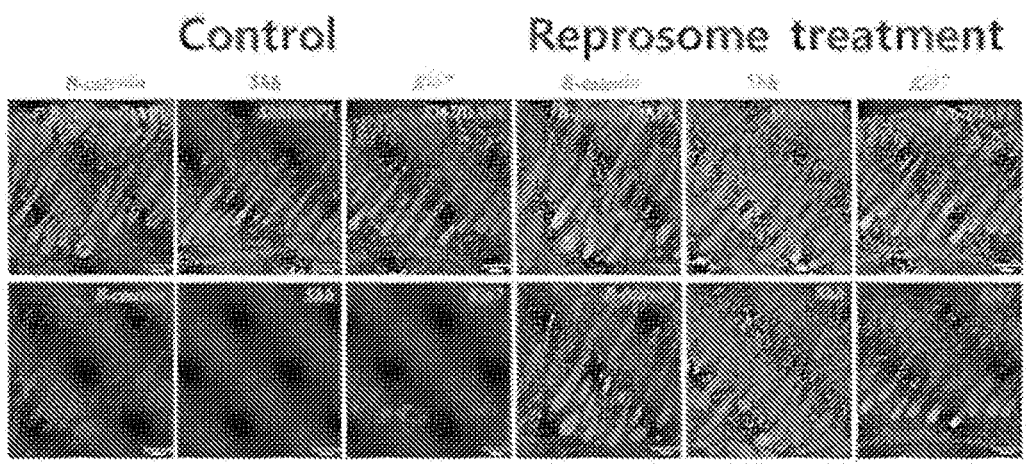
Figure 12:
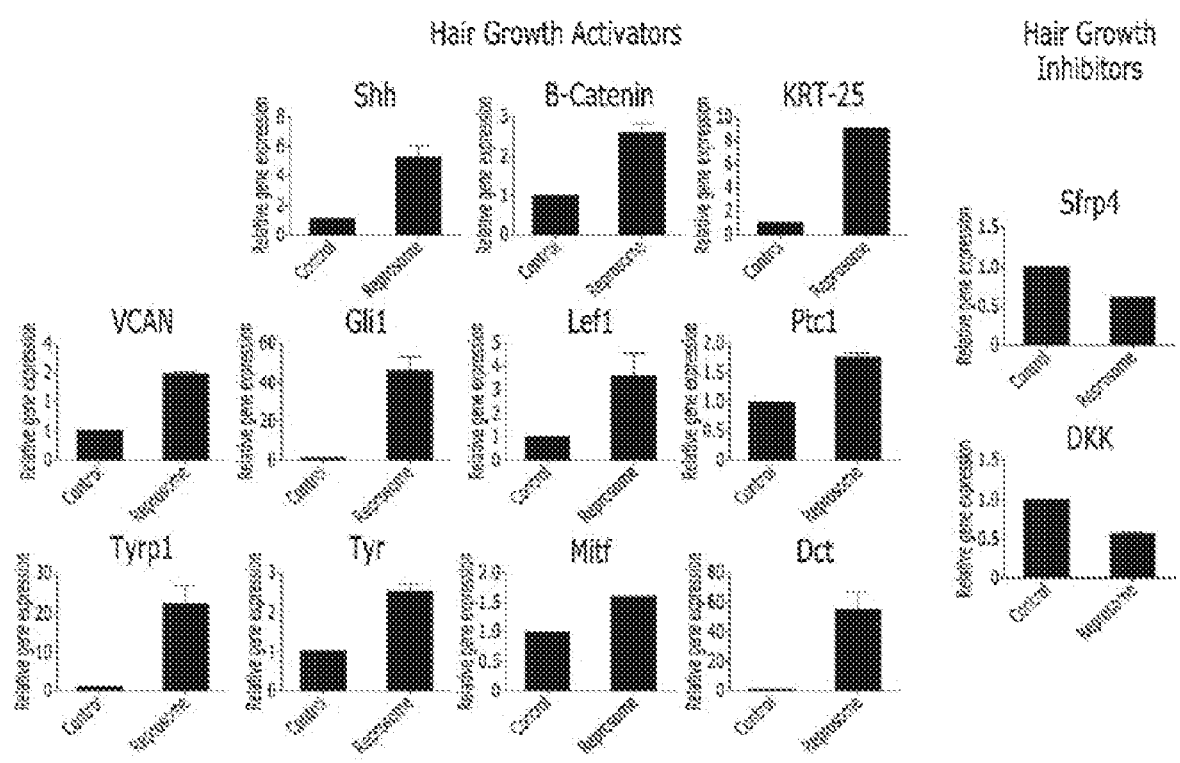
FIG. 12 depicts data showing in vivo gene expression changes in the nude mouse skin by exosomes having a hair regeneration effect according to Example 1 of the present invention, and shows mRNA qRT-PCR data related to the changes in expression of hair follicle regeneration genes by treatment with the exosomes.

As a result of H&E staining, a number of dark purple dyed portions indicating hair follicles were observed in the skin treated with the exosomes (FIG. 7A and FIG. 7B). In addition, it was confirmed that the number of hair follicles in the entire skin layer, particularly the subcutis, in the exosome-treated group, was much larger than that in the control group (FIG. 8A and FIG. 8B), suggesting that the exosomes promoted hair regeneration. As a result of applying the exosomes to the epidermis of each of nude mice and C57 mice after staining with the lipid marker Did, it was confirmed that the exosomes penetrated the pores (FIGS. 9A and 11A; counter staining was performed using the nucleus staining dye DAPI). In addition, it was confirmed through tissue immunofluorescence staining that expression of beta-catenin, Shh and Ki67 (which are proteins associated with hair follicle cell regeneration) in the exosome-treated group increased compared to that in the control group (FIGS. 9B and 11B, respectively). Furthermore, it was confirmed through qRT-PCR that expression of the hair growth promoting factors Shh, beta-catenin, KRT25, VCAN, Gli1, Lef1, Ptc1, Tyrp1, Tyr, Miff and Dct in the exosome-treated group increased, and expression of the hair growth inhibitory factors Sfrp4 and DKK in the exosome-treated group decreased (FIGS. 10 and 12, respectively). Taken together, it could be confirmed that the exosomes produced according to Example 1 exhibited an excellent effect on hair regeneration not only in vitro but also in vivo.

Comparative Example 1. Control for Exosomes Having Hair Regeneration Effect

Non-ultrasound-treated HDFs (NHDFs) were cultured in fibroblast medium (10% fetal bovine serum (Gibco)) and DMEM (Gibco) containing 1% penicillin/streptomycin (Gibco)). Isolation of exosomes (HDF-Exo) from the conditioned media of the NHDFs was performed in the same manner as the exosome isolation method of Example 1.

Comparative Example 2. Control for Mice Treated with Exosomes Having Hair Regeneration Effect D-PBS medium (the vehicle used for dilution of the exosomes before application to the mouse skin) was applied to the shaved dorsal side skin of C57 mice and the skin of nude mice without the exosomes.

The above description of the present invention is exemplary, and those of ordinary skill in the art will appreciate that the present invention can be easily modified into other specific forms without departing from the technical spirit or essential characteristics of the present invention. Therefore, it should be understood that the embodiments described above are exemplary in all aspects and are not restrictive. For example, each component described to be of a single type can be implemented in a distributed manner. Likewise, components described to be distributed can be implemented in a combined manner.

The scope of the present invention is defined by the appended claims, and it shall be understood that all modifications and alterations conceived from the meaning and scope of the claims and equivalents thereto are included in the scope of the present invention.

INDUSTRIAL APPLICABILITY

The exosomes having a hair regeneration effect according to the present invention and a composition containing the same contain large amounts of expression products of various factors capable of inducing hair regeneration, particularly genes that promote hair regeneration. In addition, the exosomes have a phospholipid-based membrane structure, and thus may easily penetrate the scalp and deliver substances with high efficiency, thus effectively inducing hair regeneration. Moreover, the exosomes do not have side effects occurring due to the use of synthetic drugs, have a longer-lasting effect, and may be used as a drug capable of ameliorating, preventing or treating hair loss.

In addition, according to the method for producing exosomes having a hair regeneration effect according to the present invention, exosomes containing high concentrations of various active ingredients having the above-described effects may be obtained in high yield through an easy process of treating cells with ultrasound stimulation.

The invention claimed is:

1. A method for producing exosomes having a hair regeneration effect in a human, the method comprising:
    a) providing ultrasound stimulation directly and indirectly to stem cells;
    b) culturing a mixture of the stem cells and a medium for a predetermined time to provide a supernatant; and
    c) isolating exosomes from the supernatant by storing the supernatant at 4° C. or below for 7 days to 1 month before filtering the supernatant through a filter;
    wherein the providing the ultrasound stimulation directly to the stem cells is applying ultrasound stimulation to a medium containing the stem cells and the providing the stimulation indirectly to the stem cells is applying ultrasound stimulation to a medium not containing the stem cells.

2. The method of claim 1, wherein the providing the ultrasound stimulation directly to the stem cells is performed with an ultrasound intensity of 0.1 w/cm$^2$ to 3 w/cm$^2$ and a frequency of 20 kHz to 20 MHz for a duration of 0.1 seconds to 20 minutes, and the providing the ultrasound stimulation indirectly to the cells is performed at an ultrasound intensity of 1 to 20 W/cm$^2$ and a frequency of 20 kHz to 20 MHz for a duration of 0.1 seconds to 20 minutes.

3. The method of claim 1, wherein the stem cells are selected from the group consisting of mammalian stem cells, progenitor cells, fibroblasts, keratinocytes and organ tissue cells.

4. The method of claim 1, wherein the medium is selected from the group consisting of an embryonic stem cell medium, a dermal papilla cell medium, and a hair follicle stem cell medium.

5. The method of claim 1, wherein the culturing of the mixture is performed for 1 hour to 10 days.

6. The method of claim 1, wherein the isolating of the exosomes is performed using a technique selected from the group consisting of ultracentrifugation, density gradient separation, filtration, size exclusion chromatography, immunoaffinity separation, precipitation, and microfluidic separation.

7. The method of claim 1, wherein the isolating of the exosomes comprises:
    centrifuging the mixture after the culturing to obtain the supernatant;
    filtering the supernatant through the filter to obtain a filtrate; and
    concentrating the filtrate.

8. The method of claim 1, wherein the isolated exosomes have a diameter of 50 nm to 200 nm.

* * * * *